United States Patent [19]

Kay

[11] 4,052,977

[45] Oct. 11, 1977

[54] METHODS OF AND APPARATUS FOR ASCERTAINING THE CHARACTERISTICS OF MOTION OF INACCESSIBLE MOVING ELEMENTS

[76] Inventor: Leslie Kay, 82 Scarborough Road, Christchurch, New Zealand

[21] Appl. No.: 596,656

[22] Filed: July 17, 1975

[30] Foreign Application Priority Data

July 15, 1974 New Zealand .......................... 174850
July 24, 1974 United Kingdom ............... 32661/74

[51] Int. Cl.² ............................................. A61B 10/00
[52] U.S. Cl. ................... 128/2 V; 73/67.5 R; 128/2.05 Z; 128/24 A
[58] Field of Search ...... 128/2 K, 2 R, 2 V, 2.05 RF, 128/2.05 S, 2.05 Z, 24 A; 73/67.5 R, 67.6, 67.7

[56] References Cited
U.S. PATENT DOCUMENTS

| | | | |
|---|---|---|---|
| 3,172,075 | 3/1965 | Kay | 340/1 |
| 3,366,922 | 1/1968 | Kay | 340/1 |
| 3,568,661 | 3/1971 | Franklin | 128/2.05 F |
| 3,572,099 | 3/1971 | Wieczorek | 73/67.7 |
| 3,631,849 | 1/1972 | Norris | 128/2.05 Z |

OTHER PUBLICATIONS

McCarty et al., "Medical & Biological Engineering", vol. 13, No. 1, Jan. 1975, pp. 59-64.
Satomura, "Journal of the Acoustical Society of America", vol. 29, No. 11, Nov. 1957, pp. 1181-1185.

*Primary Examiner*—William E. Kamm
*Attorney, Agent, or Firm*—Spencer & Kaye

[57] ABSTRACT

A method and apparatus for obtaining an audible signal containing information as to the characteristics of at least one moving element situated internally of a living body and in which a transmitting transducer fed with an electrically generated signal of supersonic frequency transmits stress waves through the body tissue to the moving element to be investigated, and a receiving transducer receives reflected waves and feeds a received electrical signal to a receiver containing a multiplier or other modulator for generating an output signal of difference frequency in the audible range, and the transmitting signal is subjected to frequency sweep and has a mean value and a sweep which produce frequency variations in the electrical difference signal arising from change of position of the element under investigation and motion of this element, the electrical difference signal being fed to a transducer for audible reproduction of a sound pattern representative of the variations of position and motion of the element.

23 Claims, 8 Drawing Figures

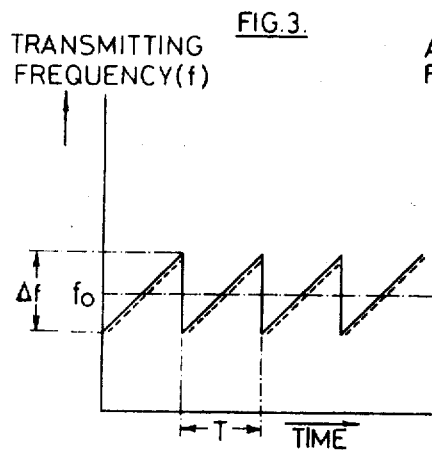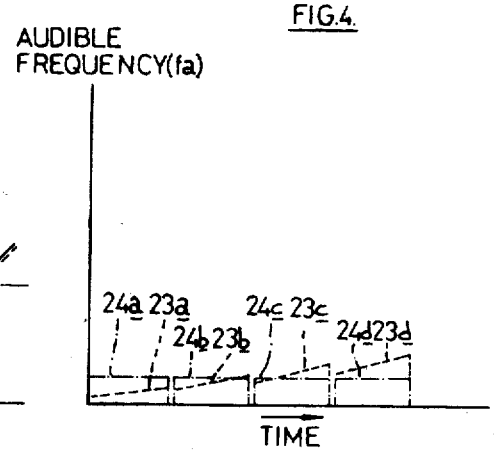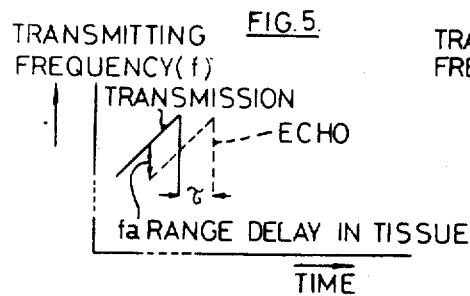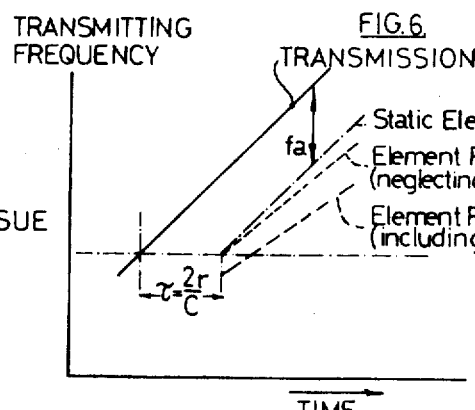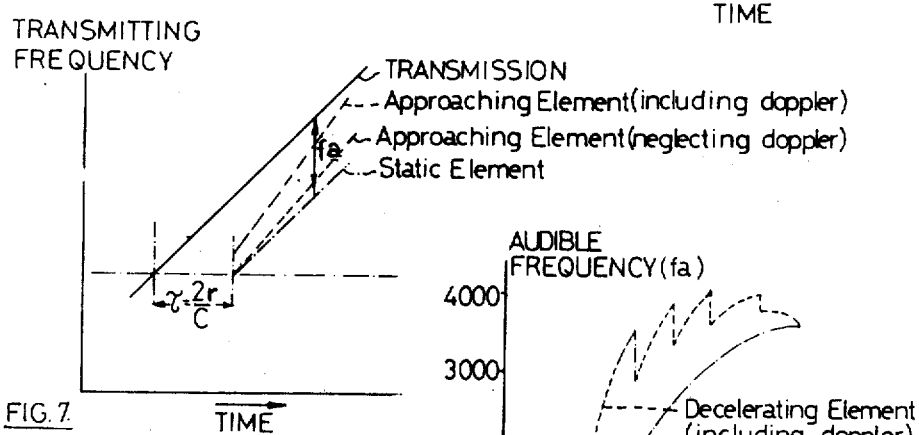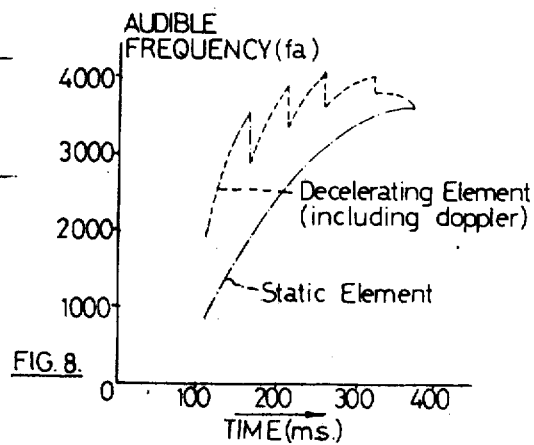

METHODS OF AND APPARATUS FOR ASCERTAINING THE CHARACTERISTICS OF MOTION OF INACCESSIBLE MOVING ELEMENTS

BACKGROUND OF THE INVENTION

This invention relates to a method of and apparatus for developing a signal containing information as to the characteristics of at least one moving element situated internally of a living body. A principal application of the invention is to obtaining information as to the characteristics of motion of the heart in a human body, but it is to be understood that the invention may be applied to the generation of a signal containing information as to the characteristics of some other inaccessible moving element of a living organism.

Such elements are normally inaccessible to the obtaining of such information in the sense that they are not visible by the use of ordinary light rays. The employment of penetrating radiation such as X-rays often requires that the element concerned be brought into contact with a medium such as a barium salt before such element can be resolved from surrounding tissue, and the latter technique is not applicable to many elements of the human body including the heart.

SUMMARY OF THE INVENTION

According to the invention a method of obtaining a signal containing information as to the characteristics of at least one moving element situated internally of a living body comprises generating an alternating electrical signal herein called the transmitting electrical signal, transducing the transmitting electrical signal into stress wave energy and radiating such energy at a transmitting station externally of the body and in a mode to be incident on the element, receiving at a receiving station externally of the body, at least part of the wave energy reflected from the element and transducing such received energy into a received electrical signal, operating on the received electrical signal to produce an electrical output signal of difference frequency as between the then transmitting electrical signal and the received electrical signal, cyclically varying the frequency of the transmitting electrical signal in a mode, and through a range of frequencies, such that the difference frequency is in the audible range and presents audibly discernible variations arising from variations in the position of the element and from motion of the element, transducing the electrical output signal into an audible output signal presenting sound pattern representative of the variations in the position and the motion of the element.

The invention further resides in the provision of an apparatus for obtaining a signal containing information as to the characteristics of a moving element situated internally of a living body, such apparatus comprising transducer means for placing externally of the body, and for transmitting stress wave energy to the moving element and receiving reflected stress wave energy from such element, means for generating an alternating electrical signal, herein called the transmitting electrical signal, for energising the transducer means to transmit the stress wave element, receiving means for receiving from the transducer means a received electrical signal in response to energisation of the transducer means by the reflected stress wave energy and including means for operating upon the received electrical signal to produce an output electrical signal of difference frequency as between the transmitting electrical signal and the received electrical signal, means for cyclically varying the frequency of the transmitting electrical signals in a mode and through a range of frequencies such that the difference frequency is in the audible range, and presents audibly discernible variations arising from variations in the position of the element and from the motion of the element, transducer means for transducing the electrical output signal into an audible output signal presenting a sound pattern representative of the variations in the position and the motion of the element.

BRIEF DESCRIPTION OF THE DRAWINGS

The performance of the method of the invention and an embodiment of the apparatus in accordance therewith will now be described, by way of example, with reference to the accompanying drawings wherein:-

FIG. 3 is a graph in which transmitted frequency of the wave energy is plotted against time;

FIG. 4 is a graph in which audible frequency derived from the heterodyne signal already referred to is plotted against time, such audible signal containing information as to the equation of motion of the heart valve under investigation;

FIG. 5 is a fragment of the graph of FIG. 3 drawn on an enlarged scale to illustrate the time relationship between the transmitted signal and the received signal or echo;

FIG. 6 is also a fragment of the graph of FIG. 3 drawn on an enlarged scale illustrating the derivation of the slope of the line representing the frequency of the received signal when the element is receding from the receiving station;

FIG. 7 is a graph similar to FIG. 6 but with the element approaching the receiving station;

FIG. 8 is a fragment of a graph similar to FIG. 4 and drawn on an enlarged scale illustrating the frequency of a typical sound pattern received from a moving element receding from the receiving station at a decreasing velocity (deceleration).

DESCRIPTION OF THE PREFERRED EMBODIMENT

Figure 1:
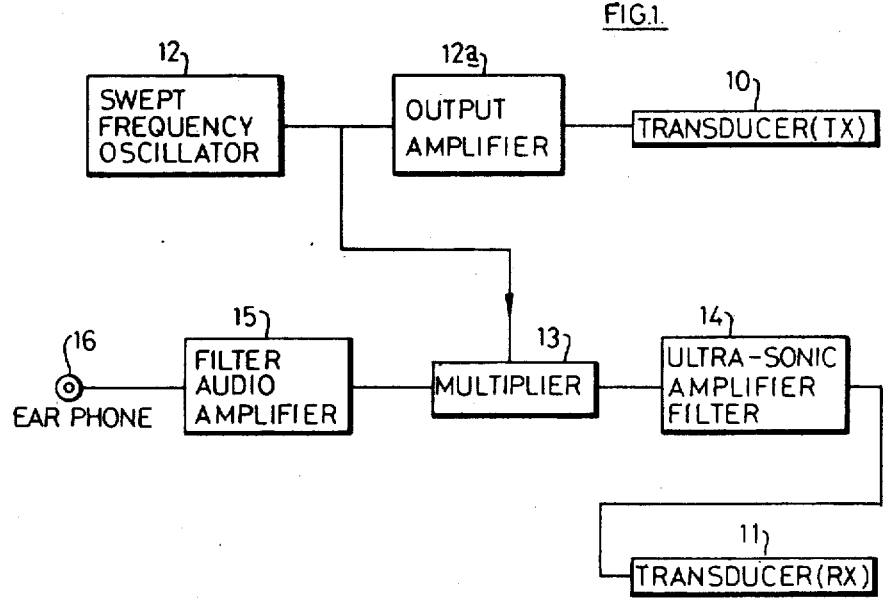
FIG. 1 is a schematic circuit diagram of one embodiment of apparatus in accordance with the invention.

The apparatus now described may be properly called an ultrasonic stethoscope for listening to the physical motion (as compared with the vibrational sounds produced in the human body by such motion) of some inaccessible element of the body, such as the heart wall and/or mitral valve of the heart. Operation of the ultrasonic stethoscope involves radiation of frequency swept ultrasonic waves (which are stress waves) by a wide band width transducer through appropriate intervening body tissue towards the part under investigation, and the receiving of reflections of this wave energy from the part by means of a suitable ultrasonic transducer, again of wide band width.

The mean value of the transmitting frequency is selected to be high enough to produce a shift of frequency on reflection from the moving element due to the Doppler effect high enough to be discernible in the audible output developed. Further, the magnitude of the frequency sweep is selected to be large enough to ensure persistence of the shortest audible signal developed (at maximum range when the frequency of the audible output should still be below the normal upper limit of audible frequency) for a sufficient time for the user to be able to discern changes of frequency due both to cyclic displacement of the moving element about its mean position and due to the motion of the element (Droppler shift). Thus the mean frequency may be at least 1 MHz and a preferred range is 1 to 10 MHz. The magnitude of the frequency sweep may be at least 0.3 of an octave or in certain cases a higher minimum may be desirable, the criterion being persistence of the audible signal developed from a given frequency sweep for at least 10 m.s. and preferably longer.

The received wave energy (converted then into an electrical signal) is processed by multiplying the received electrical signal by the transmitted signal and passing the resultant complex signal containing sum and difference frequencies through filters to pass only the difference frequency to produce an audible signal which contains information as to the position and motion (namely velocity and acceleration) of the moving element. Preferably the form in which the audible signal is developed is matched, or made as appropriate as possible, to the dynamic frequency characteristics of the human auditory neural system which then enables the observer to discriminate between different patterns of rhythmic sound, for example between a rhythmic sound characteristic of a healthy heart condition and a rhythmic sound characteristic of an abnormal or unhealthy condition. One of the underlying concepts of the invention is to utilise the exceptional ability of the sense of hearing to discriminate complex sound patterns of varying frequency, rather than merely to observe the positional change of an inaccessible element such as a part of the body using pulsed stress waves such as ultrasonic waves and a visual display having as its coordinates displacement and time.

Due to the Doppler shift of frequency upon reflection of the stress wave energy from the moving part, the frequency of the audible output signal is developed as the resultant of the static range of the element, the displacement or change of range which it undergoes during given sweep of the frequency, and the Doppler shift of frequency. This results in a sound pattern which is distinctive of a particular range and mode of motion and which can be analysed subjectively by listening to it.

Because the transmitted signal modulation or cyclic frequency variation may be made to cover a wide range of sweep ($f_o$ the mean frequency divided by $\Delta f$ the band width may typically be of the order of two), the received signal is Doppler shifted perceptibly by a greater amount at the high frequency end of its spectrum than at the low end.

The degree of frequency shift is accentuated in the audio output by reason of the use of a high value of transmitting or carrier frequency. The Doppler shift in terms of absolute frequency change depends upon the number of wave lengths contained in the distance through which the source moves in a given time. Thus, use of a high transmitting frequency (low wave length) increases the absolute Doppler shift and this absolute value is maintained after the operation producing the difference frequency. Thus, for example, a Doppler shift of 200 Hz on a radiated signal of 2 MHz is quite readily attained and translated direct to the audio band as a 200 Hz shift on the output signal which may typically be 2000 Hz.

The generation of the output signals of difference frequency as between the transmitted signal and received signal may produce a heterodyne frequency change of typically 400 Hz per cm depth of penetration of the wave energy into the body tissue. Hence an element or part under investigation, such as the mitral valve, at a depth of 5 cm. under the body surface may produce 1. an audible signal having a mean frequency of 2 kHz,
2. a change of signal frequency of, say, ± 400 Hz about the mean frequency as the valve moves between its two extreme positions,
3. superimposed on this a change of up to, say, ± 200 Hz as the valve motion varies in velocity, and
4. an additional variation as to Doppler shift of frequency is modulated by change in the incident wave length of the radiated wave energy.

A unique pattern of sound may thus be produced during a cycle of motion of the mitral valve which is characteristic of either normal movement or of one of many possible forms of disorder. It is, therefore, possible to diagnose disorders. The rhythmic change of the heart has a period of the order of 0.8 seconds and subtle variations in the sound pattern during this period can readily and meaningfully be distinguished. The human ear is very sensitive to rhythmic auditory change and is able to detect variations not readily detected by the visual process of examining visually presented display such as a variable line or like picture on the screen of a cathode ray oscilloscope. Because of the unique sound pattern produced by each moving element or part it is possible that two or more moving elements or parts may be simultaneously listened to, provided they are at different ranges (depths). Their patterns of frequency change due both to cyclic variation of range and Doppler shift will occur about different mean frequencies dependent upon the respective depths in which they are situated. Further, if their modes of motion differ this will give rise to further distinctions as between the two patterns of sound.

Conversion of the electrical output signal of difference frequency to an audible output eliminates the need for expensive visual display and recording apparatus which may thus be replaced by a miniature hearing aid earphone and/or a pocket tape recorder as the recording apparatus.

The apparatus can, therefore, be made highly portable and designed for use by a general medical practitioner as well as a specialist.

Referring now specifically to FIG. 1, the apparatus therein illustrated comprises two wide band ultrasonic transducers 10 and 11 respectively acting as a transmitter and a receiver.

Input to the transmitting transducer is derived from a frequency swept oscillator 12 feeding an output amplifier 12a which in turn is connected to the transmitting transducer.

In the receiving channel the electrical signal furnished by the transducer 11 is fed to an ultrasonic amplifier filter unit 14 and thence to a multiplier circuit 13 (or any other form of circuit producing a signal of difference frequency) and which receives a reference signal from the transmitting channel conveniently between the units 12 and 12a.

The output signal generated in unit 13 is fed through an amplifier and filter unit (low pass) 15 to cut off sum frequencies and the frequency of the oscillator 12. The output of the unit 15 is fed to a hearing aid earphone or loudspeaker 16 or to a tape or other recorder which can be used to operate unit 16.

The frequency of the carrier wave generated by the oscillator 12 and radiated by the transmitting transducer 10 may typically be between 2 MHz and 5 MHz, although higher and lower frequencies may be used depending upon the expected velocity of the element under investigation and the depth of search to be made or the depth at which the element to be investigated lies.

Figure 2:
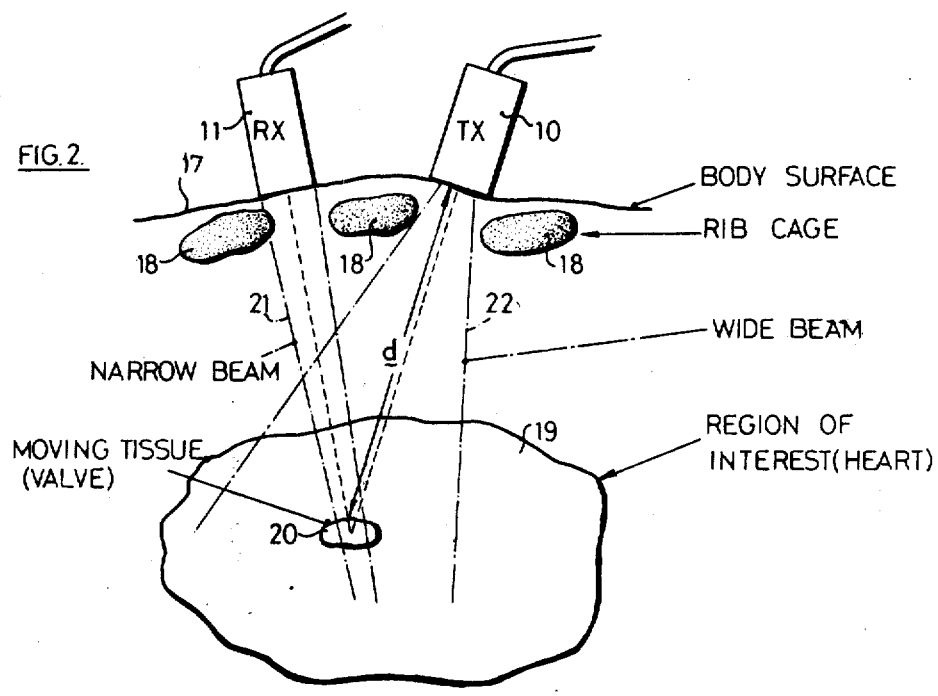
FIG. 2 illustrates the application of the apparatus (of which a portion only is shown) to the generation of an audible signal containing information as to the equation of motion of a heart valve.

As indicated diagrammatically in FIG. 2 wherein the method and apparatus is shown applied to the generation of a signal representative of the motion of a heart valve, the receiving and transmitting transducers are placed in contact with the skin and the chest of the subject, coupling being by way of conventional techniques already used in medical practice.

A portion of the subject's body is indicated diagrammatically at 17, rib cage at 18, heart at 19 and valve such as the mitral valve at 20.

The receiving transducer is preferably arranged to provide a relatively narrow beam or polar diagram, as indicated at 21, the transducer being so placed that this beam extends between a pair of ribs 18 to be incident more or less symetrically on the mitral valve 20. It will of course be understood that a single body incorporating the units 10 and 11 may be employed in certain cases.

The transmitting transducer 10 may have a polar diagram providing a wider beam, as indicated diagrammatically at 22, and is likewise placed to radiate this beam to a space between a pair of ribs 18.

The carrier wave is preferably saw tooth modulated the envelope comprising a series of time spaced rising portions and abruptly reverting portions of duration $\tau$ as indicated graphically in FIG. 3. The frequency sweep extends over a range of frequencies a plurality of times greater than the audible frequency band established at the output device or earphone 16.

The actual frequency sweep may be determined as follows. The propagation time $\tau$(FIG. 5) for travel of the ultrasonic waves along the outward path and the return path through the subject's body tissue may be of the order of 100 microseconds. This is taken to be the delay period required to produce an output signal in the multiplier 13 of 5000 Hz producing a corresponding audible frequency a at the earphone 16 or loudspeaker which is below the normal upper limit of audible frequency. However, to enable the user to appreciate the tonal quality of the audible signal produced, the duration of the audible signal should be at least 10 milliseconds and preferably longer. The ratio between such longer period, $(T-\tau)$ say, a 50 millisecond period, and the propagation period $\tau$ is 500 and hence, to obtain an output in which the tonal quality can be discerned, the frequency sweep should then be 5000 × 500 = 2.5 MHz. This is derived from the relation $\Delta f = f_a \cdot (T\tau)$ with the assumption that since $\tau$ is small compared with $T$, then $(T - \tau)$ approximates closely to T.

For all smaller values of outward and return path, $\tau$ will be smaller and the duration $(T - \tau)$ of the audible signal in each cycle will be longer.

During each period of 50 milliseconds the element or part of the body under investigation, for example the mitral valve, may move only slightly or, it at that time is situated in a rapidly moving part of its cycle of motion, may have changed position significantly with relatively high velocity. In each 50 millisecond period of the complete cycle of motion of the moving element or part, which, in the case of a heart valve, may typically be 0.8 seconds, the output difference frequency produced in the multiplier 13 and developed audibly at the output device or earphone 16 or loudspeaker will differ according to the position and the velocity of the part or element under investigation and consequently an audible signal of frequency varying throughout the cycle time of the part or element under investigation is presented to the user at the earphone 16 or loudspeaker.

If the element under investigation were stationary the difference frequency developed in the multiplier 13 and corresponding audible signal at the earphone 16 or loudspeaker would have a constant frequency dependent upon the path length through body tissue from the transmitting transducer 10 to such part or element and back to the receiving transducer 11, and such is represented diagrammatically by the chain lines 24a to 24d in FIG. 4 occurring in each of four successive frequency sweeps of the transmitted carrier. If, however, during a given frequency sweep, there is a change of position, for example leading to a decrease in path length, the output and audible frequency will decrease in magnitude. Further, since the element will have a velocity towards the receiving transducer, there will be a Doppler shift (increase) of frequency at the receiving station at which the receiving transducer is situated, thus producing a further decrease in the difference between the reference frequency (derived from the oscillator 12) and the received frequency. The two effects will thus be additive and produce an overall decrease in the audible frequency at the output device or earphone 16. If the element under investigation moves in a direction to produce increase in the path length, the positional change and the velocity of change will again be additive in producing an increase in the audible frequency developed.

In FIG. 4 there is illustrated typically a change in audible frequency over four successive 50 millisecond periods. The broken lines 23a to 23d respectively represent an approximately linear increase in the frequency of the audible note produced corresponding to constant velocity movement of the element under investigation (assumed only for simplicity of illustration) in a direction to increase the path length. The contribution to shift of frequency occurring through the Doppler effect is greater at the higher end of the frequency sweep than at the lower end (because the Doppler shift can be considered to be the number of wave lengths which can be accommodated in the distance travelled in unit time by the part or element under investigation, and the higher the carrier frequency the greater will be this number of cycles). Therefore, since this Doppler shift of frequency appears as a direct addition or subtraction in the output of the multiplier 13 and at the output device or earphone, there will be an abrupt decrease at the transition between successive 50 millisecond periods.

The unit 15 may incorporate, as mentioned, a low pass filter to eliminate unwanted sum components generated in the mixer and also unwanted frequency components due to scatter in the body tissue at depths other than that or those of interest through which the ultrasonic wave passes.

The audible sound produced at the earphone 16 or loudspeaker will thus be one of varying frequency in which a falling note denotes movement towards the receiving station, a rising note denotes movement away from the receiving station, and the rate of change of frequency denotes acceleration occurring during these movements.

Referring now to FIGS. 6 and 7, the derivation of the frequency of the received signal at the receiving transducer, i.e. the stress wave signal converted thereat into a corresponding electrical signal of the same frequency, is given by the equation:-

$$f_a(t) = \underbrace{\frac{2m}{c} r(t)}_{\text{(STATIC RANGE CODE)}} \pm \underbrace{2f_T \frac{(t)\dot{r}(t)}{c}}_{\text{(DOPPLER CHANGE)}}$$

where
- $f_a(t)$ is the time varying audible frequency. $m$ = rate of change of transmitted frequency during the linear sweep Hz/sec.
- $r(t)$ = time varying range to the moving element.
- $\dot{r}(t)$ = instantaneous radial velocity of the moving element and positive for increasing $r(t)$.
- $f_T(t)$ = frequency of the incident wave at the element due to the transmission.
- $c$ = velocity of sound propagation in the tissue.

The two terms on the right-hand side of the equation require to be added when the envelope of the frequency sweep of the transmitting signal includes time spaced rising linear portions, the intervening portions providing an abrupt reversion as illustrated typically in FIG. 3.

Under these conditions, as will be seen from FIGS. 6 and 7, the displacement which the element under examination undergoes during a frequency sweep and the Doppler effect both produce changes in the difference frequency $f_a$ which are in aiding relation, this difference frequency being increased when the element is receding from the receiving station and reduced when the element is approaching the receiving station.

For simplicity in FIGS. 3, 4, 6 and 7 it has been assumed that the mode of motion of the element under examination is one of constant velocity.

In practice cyclic movement of an element such as the mitral value of the heart will include components of acceleration and deceleration at different times and produce a difference frequency which varies in a much more complex manner as illustrated typically in FIG. 8.

In FIGS. 6 and 7 the solid line represents the transmitting frequency, the chain dotted line the frequency which would be received from the element under examination were it static, the short dashed line the frequency which would be received from the element under examination taking into account the displacement which it has undergone due to its motion but not including the change of frequency due to the Doppler effect, and the longer dashed line the frequency received from the element under examination taking into account both the displacement and the Doppler effect.

In FIG. 8 the same notation applies except that the frequencies there represented are the difference frequencies resulting from operation upon the received signal in the multiplier unit 13.

I claim:

1. A method of obtaining a signal containing information as to the characteristics of at least one oscillatorily moving element situated internally of a living body, such method comprising:

a. generating an alternating signal herein called the transmitting electrical signal;

b. transducing the transmitting electrical signal into stress wave energy and radiating such energy at a transmitting station externally of the body and spaced a distance from the element and in a direction to be incident on the element;

c. receiving, at a receiving station externally of the body, and spaced a distance from the element, at least part of the wave energy reflected from the element and transducing such received energy into a received electrical signal;

d. operating on the received electrical signal to produce an electrical output signal of difference frequency as between the then existing transmitting electrical signal and the received electrical signal;

e. sweeping the frequency of the transmitting electrical signal cyclically in sufficiently long sweeps, with a predetermined frequency vs. time pattern and sufficiently wide band frequency excursion range during each cycle so related to the distances of the transmitting and receiving stations from the element and the movement of the element that the difference frequency is in the audible range of frequencies containing an audibly discernible frequency pattern identifying variations in displacement of the position of the element and motion of the element; and f. transducing the audible range of frequencies containing such audibly discernible frequency pattern of the electrical output signal into an audible output signal.

2. A method according to claim 1 wherein the frequency sweep of the transmitting electrical signal is difined by an envelope of saw-tooth form such that the positional displacement of the moving element cyclically about its mean position, and the motion of the moving element, produce respective changes increasing the overall frequency excursion of the audible output signal.

3. A method according to claim 2 wherein the envelope comprises time spaced portions of substantially linearly rising frequency, and intervening portions reverting abruptly to a datum level.

4. A method according to claim 3 wherein the slope of the rising portions of the envelope is such that at the limit of the range of the moving element the difference frequency is still within the audible frequency range.

5. A method according to claim 1 wherein the duration of the frequency sweep of the transmitting electrical signals is such that the output signal developed at the limit of the range of the moving element has a duration long enough to enable the user to discern different sound patterns for different motion characterisitics of the element.

6. A method according to claim 5 wherein the ratio of the duration, in each cycle, of the output signal of difference frequency giving rise to the sound pattern to the transit time for the transmitted and reflected signal through the body tissue of moving element is at least 100.

7. A method according to claim 1 wherein the mean value of the frequency of the transmitting electrical signal is sufficiently high for the doppler shift of frequency in the output signal to be comparable with the shift in frequency of the output signal due to positional displacement of the moving element occurring in each frequency sweep.

8. A method according to claim 7 wherein the mean value of the frequency of the transmitting electrical signal is at least 1 MHz.

9. A method according to claim 8 wherein said value is in the range 1 to 10 MHz.

10. A method according to claim 1 wherein the magnitude of the frequency variation is such that the highest value of frequency is at least 0.3 of an octave above the lowest value.

11. A method according to claim 1 wherein the duration of the frequency sweep of the transmitting electrical signals is such that the output signal developed at the limit of the range of the moving element in response to each frequency sweep has a duration of at least 10 milliseconds.

12. Apparatus for obtaining a signal containing information as the characteristics of at least one oscillatorily moving element situated internally of a living body, comprising, in combination:
  a. means for generating an alternating electrical signal;
  b. means connected to said generating means for transducing the alternating electrical signal, as a transmitting signal, into stress wave energy and for radiating such energy at a transmitting station externally of the body and spaced a distance from the element and in a direction to be incident on the element;
  c. means disposed for receiving, at a receiving station externally of the body, and spaced a distance from the element, at least part of the wave energy reflected from the element, and for transducing such received energy into a received electrical signal;
  d. means connected for processing the received electrical signal to produce an electrical output signal at the difference frequency between the then existing transmitting signal and the received electrical signal;
  e. means connected to said generating means for sweeping the frequency of the transmitting signal cyclically in sufficiently long sweeps, with a predetermined frequency vs. time pattern and sufficiently wide band frequency excursion range during each cycle so related to the distances of the transmitting and receiving stations from the element and the movement of the element that the difference frequency is in the audible range of frequencies containing an audibly discernible frequency pattern identifying variations in displacement of the position of the element and motion of the element; and
  f. means connected to said processing means for transducing the audible range of frequencies containing such audibly discernible frequency pattern of the electrical output signal into an audible output signal.

13. Apparatus according to claim 12 wherein the means for sweeping the frequency of the transmitting electrical signal provides a frequency sweep defined by an envelope of saw-tooth form such that the positional displacement of the moving element cyclically about its mean position, and the motion of the moving element, produce respective changes increasing the overall frequency excursion of the audible output signal.

14. Apparatus according to claim 13 wherein the envelope of variation comprising time spaced portions of substantially linearly rising frequency, and intervening portions reverting abruptly to a datum level.

15. Apparatus according to claim 12 wherein the means for sweeping the frequency of the transmitting electrical signal provides a magnitude of the frequency variation such that at the limit of the range of the movable element, the output signal has a duration long enough to enable the user to discern different sound patterns for different motion characteristics of the element.

16. Apparatus according to claim 15 wherein the ratio of the duration, in each cycle, of the output signal of difference frequency giving rise to the sound pattern to the transit time for the transmitted and reflected signal through the body tissue of moving element is at least 100.

17. Apparatus according to claim 12 wherein the means for generating said transmitting electrical signal and the means for sweeping the frequency thereof provide a mean value of frequency therefor which is sufficiently high for the Doppler shift of frequency in the output signal to be comparable with the shift in frequency of the output signal due to positional displacement of the moving element occurring in each frequency sweep.

18. Apparatus according to claim 17 wherein the mean value of the frequency of the transmitting electrical signal is at least 1 MHz.

19. Apparatus according to claim 18 wherein said value is in the range 1 to 10 MHz.

20. Apparatus according to claim 12 wherein the means for sweeping the frequency of the transmitting electrical signal provides a frequency variation therefor such that the highest value of frequency is at least 0.3 of an octave higher than the lowest value.

21. A method of obtaining a signal containing information as to the characteristics of displacement and motion of at least one moving element of a living organism situated internally of a living body, such method comprising the steps of:-
  a. generating an alternating electrical signal, herein called the transmitting electrical signal, and which is of ultrasonic frequency, transducing the transmitting electrical signal into stress wave energy, and transmitting such stress wave energy along a path extending from a transmitting station at the surface of said body to said element,
  b. receiving at a receiving station, also at the surface of said body, at least part of the wave energy reflected from the element along a path therefrom to said receiving station and frequency shifted by Doppler effect and time shifted by transit along said paths, and transducing said received energy into a received electrical signal,
  c. combining said Doppler shift of frequency and said time shift into a single resultant frequency shift by an intermodulating operation between a succession of frequency sweep electrical signals generated for said operation, the transmitting electrical signal, and the received electrical signal, and selectively filtering the intermodulation products to derive an electrical output signal of audible frequency persisting over each of a plurality of successive but time spaced periods in each of which change of position and change of motion of the element is reflected as a combined or resultant frequency change,
  d. and transducing said electrical output signal into an audio output signal.

22. A method according to claim 21 wherein:- a. the intermodulation operation comprises applying the frequency sweep signal to sweep the frequency of the electrical transmitting signal, and deriving a difference frequency signal between the swept frequency electrical transmitting signal and the delayed and Doppler shifted received electrical signal, b. the frequency of the transmitting electrical signal, and the duration and magnitude of the sweep signal, are selected respectively to provide a Doppler shift of frequency which is comparable or significant in relation to that produced in the output signal by said time delay in said paths, and to provide a duration for said time spaced periods in which the transduced electrical output signal persists at least great enough for recognition of different sound patterns.

23. A method according to claim 21 wherein the duration of each period in which said audible output signal persists is at least 10 milliseconds.

* * * * *